US012799178B2

(12) United States Patent
Orvar et al.

(10) Patent No.: US 12,799,178 B2
(45) Date of Patent: Nov. 17, 2026

(54) GROWTH FACTOR COMPOSITION FOR CELL CULTURE-PRODUCED MEAT

(71) Applicant: ORF LIFTAEKNI HF, Kopavogur (IS)

(72) Inventors: Bjorn Larus Orvar, Reykjavik (IS); Arna Runarsdottir, Reykjavik (IS); Jon Mar Bjornsson, Hafnarfjördur (IS); Hilmar Vidarsson, Reykjavik (IS)

(73) Assignee: ORF LIFTAEKNI HF, Kopavogur (IS)

( * ) Notice: Subject to any disclaimer, the term of this patent is extended or adjusted under 35 U.S.C. 154(b) by 892 days.

(21) Appl. No.: 18/000,724

(22) PCT Filed: Jun. 7, 2021

(86) PCT No.: PCT/IS2021/050008
§ 371 (c)(1),
(2) Date: Dec. 5, 2022

(87) PCT Pub. No.: WO2021/245711
PCT Pub. Date: Dec. 9, 2021

(65) Prior Publication Data

US 2023/0220027 A1 Jul. 13, 2023

(30) Foreign Application Priority Data

Jun. 5, 2020 (IS) .................................... IS 050305

(51) Int. Cl.
*C07K 14/425* (2006.01)
*C07K 14/475* (2006.01)
*C12N 5/077* (2010.01)
*C12N 15/82* (2006.01)

(52) U.S. Cl.
CPC .......... *C07K 14/475* (2013.01); *C07K 14/425* (2013.01); *C12N 5/0658* (2013.01); *C12N 5/0659* (2013.01); *C12N 15/8257* (2013.01); *C12N 2501/10* (2013.01)

(58) Field of Classification Search
CPC .. C07K 14/475; C07K 14/415; C07K 14/425; C12N 5/0658; C12N 5/0659; C12N 15/8257; C12N 2501/10
See application file for complete search history.

(56) References Cited

U.S. PATENT DOCUMENTS

2004/0078851 A1 4/2004 Huang et al.
2007/0143872 A1* 6/2007 Orvar ................. C12N 15/8234 800/278
2010/0015713 A1* 1/2010 Deeter ............... C12N 15/8257 435/405
2012/0315697 A1* 12/2012 Pettit .................... C12N 5/0056 435/375
2019/0024104 A1 1/2019 Herman et al.

FOREIGN PATENT DOCUMENTS

AU 2012202697 B2 5/2012
WO 9931223 A1 6/1996
WO 2007002762 A2 1/2007
WO 2009020389 A1 2/2009
WO 2010001417 A2 1/2010
WO 2010001418 A1 1/2010
WO WO-2010096588 A2 * 8/2010
WO 2011083500 A2 7/2011

OTHER PUBLICATIONS

Gomes et al. "Prospects for the Production of Recombinant Therapeutic Proteins and Peptides in Plants: Special Focus on Angiotensin I-Converting Enzyme Inhibitory (ACEI) Peptides" in Genetic Engineering—A Glimpse of Techniques and Applications, publ Feb. 22, 2019; www.intechopen.com/chapters/65771; 29 pages.*
Xu et al. Green factory: Plants as bioproduction platforms for recombinant proteins. Biotechnol Adv 30: 1171-1184, 2012.*
Erlendsson et al. Barley as a green factory for the production of functional Flt3 ligand. Biotechnol J 5: 163-171, 2010.*
Magnusdottir et al., "Barley grains for the production of endotoxin-free growth factors," Trends in Biotechnology, 2013, vol. 31(10): pp. 572-580. Abstract only.
Specht et al., "Opportunities for applying biomedical production and manufacturing methods to the development of the clean meat industry," Biochemical Engineering Journal, 2018, vol. 132: pp. 161-168.
Helgi, Cell Structure: Disrupting the Meat Industry, 2021, https://www.openaccessgovernment.org/plant-biotechnology/107076/.
International Search Report and Written Opinion of International Application No. PCT/IS2021/050008, mailed on Sep. 22, 2021, 15 pages.
Iceland Search Report of International Application No. PCT/IS2021/050008, completed on Oct. 23, 2020, 2 pages.
Datar et al., "Possibilities for an vitro meat production system," Innovative Food Science and Emerging Technologies, 2010, vol. 11: pp. 13-22.
Gaydhane et al., "Cultured meat: state of the art and future," Biomanufacturing Reviews, 2018, vol. 13(1): pp. 4-5.

* cited by examiner

*Primary Examiner* — Bridget E Bunner
(74) *Attorney, Agent, or Firm* — HESLIN ROTHENBERG FARLEY & MESITI P.C.

(57) ABSTRACT

The invention relates to the use of a growth factor composition comprising one or more recombinant animal growth factor and one or more plant seed protein for cultivating cells for the production of cell culture meat. The invention also relates to a method of cultivating cells for the production of cell culture meat using a growth factor composition that comprises one or more recombinant animal growth factor and one or more plant seed protein.

4 Claims, 5 Drawing Sheets

GROWTH FACTOR COMPOSITION FOR CELL CULTURE-PRODUCED MEAT

CROSS REFERENCE TO RELATED APPLICATIONS

This application is a U.S. National Phase filing under 35 U.S.C. § 371 of International Application PCT/IS2021/050008, filed Jun. 7, 2021, and published as WO 2021/245711 A1 on Dec. 9, 2021. PCT/IS2021/050008 claims priority from Iceland application number IS 050305, filed Jun. 5, 2020. The entire contents of each of these prior applications are hereby incorporated herein by reference in their entirety.

FIELD OF INVENTION

The present invention is within the field of cell culture technology and specifically the emerging field of production of meat or meat-like food products via cell culture.

TECHNICAL BACKGROUND

Cultured meat production is an emerging and innovative technology for producing animal meat from cultivated tissue using tissue engineering instead of conventional rearing of farm animals for slaughtering. This approach involves the cultivation of animal cells that are made to grow into muscle tissue and fat cells. With this technology, protein-rich food products are obtained that are materially and nutritionally equivalent to conventional meat- and fish-based foods. The technology is seen as a promising opportunity to reduce the need for conventional rearing of farm animals, which besides obvious animal welfare concerns is very resource-demanding, with ever increasing water and land-use for growing feed crops. It will also diminish many of the negative consequences of conventional meat production, including greenhouse gas emissions, deforestation, pollution, and antibiotic resistance.

Due to growing awareness of the ecological footprint of meat production and increasing concerns of animal welfare, state-of-the-art solutions to replace or reduce conventional meat consumption with "lab cultured meat", a term also known as "in vitro meat", "clean meat" or "cell cultured meat" (CCM) have been proposed. It is a consensus within the research community that culturing meat in a laboratory using already established methods from regenerative medicine and tissue engineering is a promising approach to create CCM.

It is estimated that in 2040 as much as 35% of global meat consumption will be CCM. This trend is driven by animal welfare issues and the need to reduce the environmental impact of traditional meat production.

Current methods of livestock production are relatively inefficient and the conversion rate of feed to animal protein is low, or about 1.9% for beef and 13% for pigs. By contrast, scaled-up CCM requires an estimated 225 g of nutrients (amino acids, glucose, etc.) to produce the same 200 g of protein. Thus, CCM production is predicted to be about 30-45× more efficient than conventional beef production.

The CCM trend is also driven by increased demand and consumption of meat in Asia, especially in China. In fact, the Food and Agriculture Organization of the United Nations (FAO) estimates that the demand for meat is going to increase by 70% by 2050, to reach 470 million tons, and that current production methods are not sustainable. In fact, the world is approaching a crisis due to rapid increase in consumption of meat and other animal-based proteins which in turn calls for a large amount of feed.

Overall, the driving force behind the development of CCM is 1) the rapidly growing demand for meat in the world, 2) increased concerns about the environmental impact of meat production and 3) the growing concerns about animal welfare associated with intensive livestock production. This has led to a rapidly emerging market for alternative meat products, such as CCM, as consumers want to reduce consumption of meat due to high cost, animal welfare or environmental issues.

To date, however, although "prototype" laboratory meat in meal size units has been produced successfully, costs are much too high for the technology to become viable for commercial production.

A very significant cost factor in the cell culture production of meat arises from the need of significant quantities of specialised cell culture media and in particular the need for suitable growth factor proteins that tend to be the most expensive components of cell culture media. Currently, the cost of CCM production is to a large extent (up to 90%) driven by cost of growth factors, making the production economically not viable.

SUMMARY OF INVENTION

The present invention is based on the discovery, at least in part, that certain, native plant seed proteins can protect and improve the storage time of purified growth factors (GFs), if included in the purified, final product. The invention is also based, at least in part, on the discovery that these native, seed proteins can improve the bioactivity of the growth factor in cell culture media and thus improve the qualities of the cell culture media.

Furthermore, including these seed proteins in the final product can reduce downstream processing cost dramatically. With the financial benefit of ease of scaling up plant crops, effective yield and lower downstream processing costs, overall cost saving can be up to 1000-fold, eliminating the largest obstacle in the CCM production, which is the cost of growth factors.

An object of the invention is to provide improved growth factor compositions and supplements that are particularly useful in the generation of cell cultured meat (CCM). The object is achieved in accordance with the invention as described and claimed herein.

Growth factors can either be sourced from a native source or produced recombinantly in a transient or transgenic host organism. Plant seed-based production of recombinant growth factors has many advantages for cell culture media for meat production. It is an endotoxin-free, easily scalable, inexpensive production platform, the seed is a natural, long-term storage vehicle for the recombinant growth factors making stockpiling easier, less costly and more logistical prior to downstream processing. Additionally, plant-based production of growth factors as described herein can be arranged fully animal-free, i.e. fully made without any biomaterials taken from animals, which is very beneficial to a large segment of consumers of prospective CCM products.

Accordingly, in a first aspect the invention relates to a growth factor composition or supplement, comprising one or more recombinant animal growth factor and one or more plant seed protein for cultivating cells for the production of cell culture meat. The recombinant animal growth factor can be plant-derived, i.e. the recombinant animal growth factor can be produced in transgenic plants.

The invention also relates to a method of cultivating cells for the production of cell culture meat, the method comprising (a) providing at least one cell culture that is capable of growing to generate a meat-like tissue, and (b) supplying said at least one cell culture with a growth medium for sustaining growth and/or cell differentiation of said cell culture, the method being characterised in that said growth medium comprises at least one growth factor composition that comprises one or more recombinant animal growth factor and one or more plant seed protein.

The invention also relates to growth factor supplements. Thus, a further aspect relates to a growth factor supplement, in particular a growth factor supplement for use in the cultivation of cells for the production of cell culture meat. The growth factor supplement preferably comprises an extract from transgenic plant seed material selected from the group consisting of barley, wheat, oat, rye, maize, rice, soya, peas, millets, sorghum and rape. The extract preferably comprises in the range from about 0.1% to about 97% by weight of one or more recombinant animal growth factor expressed in said plant.

Yet a further aspect of the invention relates to the use of a growth factor composition comprising one or more recombinant animal growth factor and one or more plant seed protein for cultivating cells for the production of cell culture meat, wherein the growth factor composition is from a non-animal source and preferably produced in a transgenic plant. The growth factor composition being used is preferably a growth factor composition as described and defined herein.

Another aspect of the invention sets forth a cell culture medium comprising a growth factor supplement of the invention, in particular a cell culture medium for the cultivation of cell culture meat (CCM). The cell culture medium can be defined and referred to as a growth factor medium. Accordingly, the cell culture medium of the invention preferably comprises a growth factor supplement as described herein, comprising an extract from transgenic plant seed material selected from the group consisting of barley, wheat, oat, rye, maize, rice, soya, peas, millets, sorghum and rape, as described herein.

Yet another aspect provides a kit comprising (a) a cell culture medium, in particular a cell culture medium for cultivating cells for the production of cell culture meat; and (b) growth factor supplement as described and defined herein, for sustaining growth of said cells. Accordingly, the kit can comprise an extract from transgenic plant seed material selected from the group consisting of barley, wheat, oat, rye, maize, rice, soya, peas, millets, sorghum and rape, the extract preferably comprising in the range from about 0.1% to about 97% by weight of one or more recombinant animal growth factor expressed in said transgenic plant.

As used herein, the term "cell cultured meat", abbreviated as CCM, refers to meat that is generated through in vitro cultivation of animal cells, replacing slaughtered animals. The term is sometimes also referred to as "cultured meat", "lab cultured meat", "in vitro meat", or "clean meat".

As used herein, the term "non-animal" should be understood as not relating to or not being derived from animals. The compositions disclosed herein are non-animal, i.e. the compositions are not derived from animals, neither directly nor indirectly.

As used herein, the term "endotoxin-free" should be understood as meaning that there are no measurable endotoxins present and preferably endotoxin-free substances and compositions are derived from organisms that do not produce endotoxins.

The growth factors (GFs) can preferably be plant-made or plant-derived animal GFs, meaning that the GFs are animal GFs produced (expressed) in transgenic plants.

DETAILED DESCRIPTION

Figure 1:
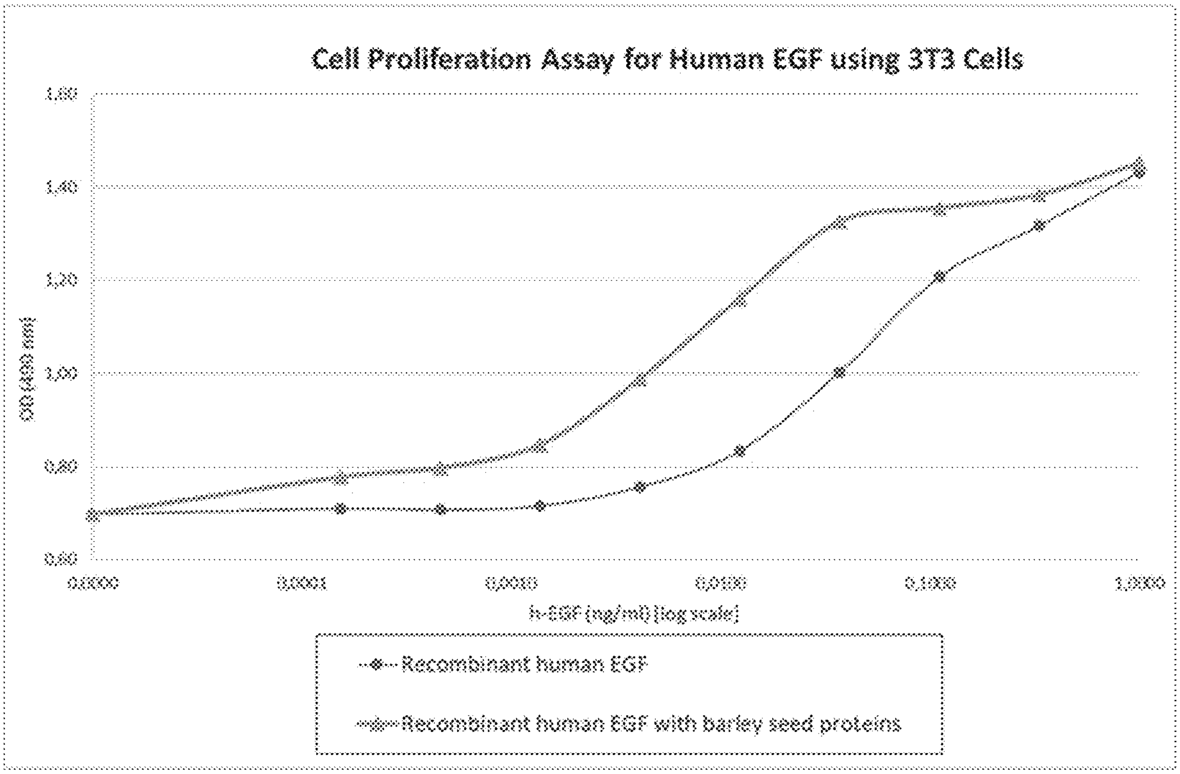
FIG. 1: Results of cell proliferation assay of 3T3 cells grown in medium with plant-expressed recombinant EGF with and with barley seed proteins.

The growing demand for meat as well as the increasing concerns about the environmental impact of meat production have catalysed innovation in meat-like production, such as cell culture meat (CCM), where the environment and the animal welfare are the focal point. However, for CCM to be a realistic alternative to meat it must fulfil several requirements:

a) be at least as good or better (taste and texture) than the conventional animal-based meat; b) reach similar consumer price (or lower) than conventional animal-based meat;

c) be available in quantities necessary for the world market;

d) be as nutritionally as good or better than conventional animal-based meat;

e) fulfil requirements for animal welfare;

f) be more environmentally sustainable than conventional animal meat production.

At present it is clear that CCM is already able to fulfil many of these, including e) and f) with 99% less water consumption and 93% less land and less greenhouse-gas emission than in conventional animal farming.

CCM production however requires large amounts of animal GFs at a low price as a part of the culture media. At present, world-wide producers of GFs cater for the R&D market or the pharmaceutical market in small, pilot scale amount. Production costs are high, and the GFs are sold at prices ranging from hundreds to thousands of EUR per milligram. These prices are prohibitive for CCM production and constitute a major bottleneck for the emerging CCM sector as these prices lead to a production cost of cell-cultured meat amounting hundred to thousands of EUR per kg meat. GFs represent up to 90% of the cell culture media cost. It is inconceivable to develop the technology and business of CCM unless GFs can be produced and delivered at costs approximately 100-1000 times lower than present day prices and in the large quantities required for the future CCM production.

Hence, economical large-scale production of low-cost GFs is of great importance for the world if it is to adopt CCM production, due to the very high proportion of GF cost in CCM production, resulting at present in an essentially non-marketable product.

The present invention addresses these issues, by providing cell culture GF compositions, provided as e.g. GF supplements, that can be produced at a substantially lower cost than present GF solutions. Using the GF solutions disclosed herein, CCM production becomes economically viable.

Another advantage of the invention relates to modified downstream processing for co-purification of certain native storage proteins with the GF that can dramatically reduce the downstream processing cost to levels critical for commercial production of GFs for cell culture production of meat. These native plant storage proteins quite surprisingly turn out to have very beneficial and surprising stabilizing effects on the overexpressed GFs. This means that utilising simple co-purification schemes that provide growth factors co-purified with one or more native seed proteins and typically a group of such proteins, not only do the purification processes for the plant-expressed GFs become simpler and less costly compared to more rigorous purification steps necessary for typical expression systems and in particular when using bacterial systems, but at the same the resulting GF extracts have desired characteristics and surprising advantages over more highly purified GFs without such co-purified plant proteins.

Accordingly, in one aspect, the invention relates to a process that includes one or more, preferably all, of the following steps in order: harvesting the seeds; clean the seeds with seed cleaning or seed sorting machine; de-hulling the sorted seeds; sterilizing the de-hulled seeds and milling to fine powder; extracting total soluble proteins in extraction buffer; clarifying the extract; selecting suitable purification for co-purification of GFs and seed proteins, such as selecting specific affinity using for example affinity chromatography; buffer exchange and fill and finish.

Accordingly, in one embodiment, the invention relates to a process that includes one or more, preferably all, of the following steps in order: harvesting the seeds; clean the seeds with seed cleaning or seed sorting machine; de-hulling the sorted seeds; sterilizing the de-hulled seeds and milling to fine powder; extracting total soluble proteins in extraction buffer; clarifying the extract; co-purification of GFs and seed proteins with suitable purification steps such as with size-fractionation using different filtration steps; buffer exchange and fill and finish.

A growth factor seed extract according to the invention can be suitably prepared by milling harvested transgenic seeds containing the desired recombinant growth factor in a mill to obtain fine powder (flour). The ground/milled material may optionally by processed chemically or enzymatically, to enhance release of the desired transgenic protein, such as with enzymatic treatment with one or more enzymes selected from beta-glucanase, amylase, xylanase or cellulase. Optimized extraction buffer can then be added to the milled flour and the resulting solution is mixed well (e.g. by stirring). The extraction buffer may be suitably selected from but is not limited to conventional aqueous buffers such as phosphate buffer, TES (2-{[tris(hydroxymethyl)methyl]amino}ethanesulfonic acid), TRIS tris(hydroxymethyl)-aminomethane, MES (2-(N-morpholino)ethanesulfonic acid), HEPES ((4-(2-hydroxyethyl)-1-piperazineethane-sulfonic acid)), MOPS (3-(N-morpholino)propanesulfonic acid), ADA, etc. and mixture thereof. The buffers may further comprise salts and further ingredients conventionally used in protein purification buffers that do not interfere with the extraction process.

In some embodiments solids may be separated from the liquid extract such as by centrifugal force and the supernatant harvested.

The GF extract thus obtained can conveniently be mixed in conventional cell culture media such as those herein described, in particular those that are suitable for cell culture meat production.

An initial crude transgenic seed extract thus obtained can be processed further by further purification and concentration. One example of a useful chromatography purification comprises adding to the extract an IMAC chromatography resin that effectively binds the growth factor, when a poly-His tag has been added thereto (with conventional biotechnology methods known to the skilled person). Other useful affinity tags may as well be used, with appropriate affinity purification, such as but not limited to using repetitive HQ sequence, streptavidin tag, polycystein tag, PDZ ligand, FLAG epitope, Glu-Glu tag, etc. which are as such well known to the skilled person. The mixture of extract and resin is stirred in appropriate buffer, thereafter the IMAC resin (or other affinity resin) can be separated from the liquid by centrifugation. The liquid phase is discarded and the resin resuspended in appropriate washing buffer and spun down and the liquid phase decanted off the resin. The washing is repeated as needed. The resin is resuspended in appropriate elution buffer and after centrifugation the supernatant is decanted off the resin and typically run through gel filtration chromatography (desalting) for buffer exchange. Other useful chromatography techniques may be used alternatively or additionally, such as ion exchange chromatography and size-exclusion chromatography. Column chromatography may used with any of these techniques but other techniques are as well applicable, such as expanded bed chromatography.

In order to realistically mimic the native muscle tissue, cells and biomaterial must be combined under correct conditions to form a mature tissue, a process where GFs are crucial additives. In addition, to meet consumers acceptance CCM must also mimic the conventional meat qualities such as physical appearance, smell, texture and taste. Therefore, it is important that CCM contains not only skeletal muscle cells, but also other key components of the muscle tissue, including components of the connective tissue, microvascular networks and fat tissue (Pandurangan et. al. 2015). The techniques used to address these challenges is the tissue engineering technology that combines the scaffold-based technique, using edible scaffolds, and the co-culture technology, using multiple cell culturing protocols in which all tissue-relevant cell types are co-cultured to form coherent muscle tissue structure (Kosnik et. al. 2003; Edelman et. al. 2005).

Different stem cell types have been used in CCM production, including Embryonic Stem cells (ESc), induced Pluripotent Stem cells (iPSc), satellite muscle stem cells (myoblasts) and other adult stem cells (i.e mesenchymal stem cells and adipose stem cells). Satellite cells are population of progenitor cells, located at the periphery of skeletal myofibers and are the main cell source for muscle tissue maintenance (Peault, et. al. 2007).

Currently, satellite stem cells, isolated and cultured from muscle biopsies are considered the most suitable cell source for CCM production (Post et. al., 2012). Satellite cells have been successfully isolated from muscle of several animal species for CCM production, including bovine (Dodson, et.

al. 1987), chicken (Yablonka-Reuveni, et. al. 1987), lamb (Dodson, et. al. 1986) and porcine (Blanton, et. al. 1999).

One of the best characterized and most widely used satellite cell models for investigating muscle regeneration is the mouse myoblast stem cell line C2C12 (Germani, et. al. 2003). The C2C12 myoblasts have been the main cell model applied for studying the effect of biomaterials, including GFs on muscle growth (Ben-Arya et. al. 2019). Satellite cells isolated from muscle biopsies of livestock animals for CCM are tissue specific stem cells which do not possess pluripotent phenotype, and as such do not have the ability to proliferate unlimitedly in culture (Peault, et. al. 2007). Until recently, the general concerns were that no stable, characterized cell line from livestock animals existed. Fortunately, for the CCM production sector, a group of scientists now successfully managed to establish a stable pluripotent cell line from bovine blastocysts (Bogliotti et. al. 2018), and their success will unquestionably facilitate generation of more stable cell lines from livestock animals. The PS have also received attention as a possible cell source for CCM production. PS cells are extensively studied and they could be valuable factor in lowering production cost of CCM, by reducing time and effort of the constantly recurring events of stem cells generation from animal biopsies (Kadim, et. al. 2015). In fact, few CCM companies are betting on them as the cell source for CCM.

The ideal culturing medium for CCM production should be chemically defined, formulated with accurately selected nutrients and GFs, and be free of animal sources (Sharma et. al. 2015). GFs are natural regulators of stem cells proliferation and differentiation, and their biological importance for stem cell research is indisputable (Ribeiro, et. al. 2010). GFs, in combination with other biomaterials, are already extensively utilized for culturing muscle stem cells for various tissue engineering applications, including CCM production. Using satellite cell lines such as the C2C12 myoblasts, several GFs have been identified as major players in regulation of muscle growth and regeneration (Perry et. al. 2000).

To date, numerous animal-free and serum-free cell media products are already commercially available for CCM production, a result of substantial advancements within the field of regenerative medicine research in the last 20 years (Specht, et. al. 2018). However, despite the wealth of scientific evidence accumulating within stem cell research in recent years, CCM is not yet ready for public consumption, mostly due to the extremely high production cost of CCM that must be addressed before large-scale production can be achieved. A major hindrance is the cost of GFs which is estimated to be around 99% of media cost (Ben-Arye et. al. 2019). Therefore, GFs need to be much less expensive, they should come from animal-free source, and preferably also from an endotoxin-free source (non-bacterial).

Currently, the GFs available for the CCM are made in bioreactor with animal cells, bacteria or yeast. These production systems are both too expensive and difficult to scale up, as well as being animal-derived, not endotoxin-free (e.g. from *E. coli*), or have problems with activity in cell cultures (hyper-glycosylation/unproper post-translational modification). These systems do not provide as inert environment for recombinant protein production as plant seeds do and may, therefore, require that the GF is purified to higher purity levels beyond what is needed for GFs produced in crop seed production systems such as barley or rice. In addition, these present available systems may also have problems with public perception which is important in marketing of CCM. However, these important criteria make GFs production in transgenic plants an attractive alternative, which would make mass production of clean and cost-effective GFs possible (Pandurangan, et. al. 2015).

Plants have sophisticated mechanisms at the cellular and molecular levels to combat biotic and abiotic stress. One of the consequences of abiotic stress is the denaturation and aggregation of cellular proteins leading to cell death. The chaperone-like activity of cytochromes (CYPs) and their role in the rate-limiting step of protein folding by peptidyl prolyl bond isomerization is associated with their involvement in stress responses. Expression of many plant CYPs is induced in response to stress suggesting their possible function in stress tolerance. For example, expression of the *Arabidopsis* CYP, ROTAMASE CYCLOPHILIN 1 (ROC1), increases upon wounding. Similarly, maize and bean CYP gene expression increases in response to heat stress, wounding, high salinity, or low temperature (Mainali, H. R. et. al. 2017). These and other findings demonstrate a role for plant CYPs in stress tolerance. Thus, CYP proteins, such as cyclophilin and related proteins, are examples of plant proteins that can be very helpful as co-ingredients with GFs expressed in plants.

Orthodox seeds are seeds that survive drying and/or freezing during ex-situ conservation. The end of orthodox seed development is typified by a developmentally regulated period of dehydration leading to the loss of bulk water from the entire structure. During desiccation, mature orthodox seeds reach levels of 5-10% water and can frequently be dried further to 1-5% water with little or no loss of viability. When dehydration occurs, the cytoplasm condenses and intracellular components become more crowded. These conditions provide an environment for numerous undesirable interactions that can lead to protein aggregation and denaturation as well as organelle-cell membrane fusion (Hoekstra et al. 2001). Acquisition of desiccation tolerance, or the ability to withstand these very low water potentials and subsequent molecular crowding, has been correlated with the accumulation of various protective compounds including proteins (and sugars).

Two classes of proteins most likely to make a major contribution to cellular stability in mature seeds include the small heat shock proteins (HSPs) and the late embryogenesis abundant (LEA) proteins. Small HSPs, that accumulate late in seed development, may help minimize the aggregation effects of cytoplasm condensation by acting as molecular chaperones and thereby contribute to stabilization of a glassy state. LEA proteins are a diverse class of highly abundant, heat-stable proteins that accumulate late in embryo maturation and during the developmentally regulated period of dehydration at the end of seed development. Many studies have reported that dehydrins may play a protective function on enzymes or phospholipids as molecular chaperone or molecular shield.

Dehydrins (DHNs), or group 2 LEA (Late Embryogenesis Abundant) proteins, play a fundamental role in plant response and adaptation to abiotic stresses. They accumulate typically in maturing seeds or are induced in vegetative tissues following salinity, dehydration, cold and freezing stress. It is therefore possible that some LEAs have a dual role during the plant life cycle, and function as a storage protein during germination as well as in desiccation tolerance during seed development.

Although the vast majority of the individual proteins present in mature seeds have either metabolic or structural roles, all seeds also contain one or more groups of proteins that are present in high amounts and that serve to provide a store of amino acids for use during germination and seedling growth.

Despite wide variation in their detailed structures, all seed storage proteins have a number of common properties. First, they are synthesized at high levels in specific tissues and at certain stages of development. In fact, their synthesis is regulated by nutrition, and they act as a sink for surplus nitrogen. However, most also contain cysteine and methionine, and adequate sulfur is therefore also required for their synthesis. Many seeds contain separate groups of storage proteins, some of which are rich in sulfur amino acids and others of which are poor in them.

A second common property of seed storage proteins is their presence in the mature seed in discrete deposits called protein bodies. Finally, all storage protein fractions are mixtures of components that exhibit polymorphism both within single genotypes and among genotypes of the same species.

The total protein contents of cereal seeds vary from about 10-15% of the grain dry weight, with about half of the total being storage proteins. Cereal seed storage proteins are produced by the secretory pathway and deposited in discrete protein bodies.

Thus, certain plant proteins are believed to result in increased stability and response to stress, including dehydrins, protease inhibitors, hordeins, late-embryogenesis abundant proteins, (LEA), cyclophilins, ABA-responsive proteins, globulins, albumins, prolamins, vicilins, glutelins, and zeins.

A consequence of the capability of orthodox seeds to survive extreme conditions is the increased stability of proteins present in those seeds. This is manifested by transgenic proteins expressed in plants, for example barley, wheat, oat, rye, maize, rice, soya, peas, millets, sorghum and rape. Thus, proteins that are expressed in such plants and stored in seeds are found to maintain their stability and bioactivity over prolonged periods of time. As consequence, the production of proteins in plant seeds is particularly advantageous, as the environment in the plant seeds confers increased stability to the proteins.

It can be particularly advantageous to express bioactive proteins such as GFs in plant seeds, including for example the GFs Keratinocyte Growth Factor (KGF), Vascular Epithelial Growth Factor (VEGF), Fibroblast Growth Factors basic (bFGF), Fibroblast Growth Factors acidic (aFGF), Fibroblast Growth Factor-9 (FGF9), Fibroblast Growth Factor-16 (FGF16), Fibroblast Growth Factor-19 (FGF19), Fibroblast Growth Factor-20 (FGF20), Fibroblast Growth Factor-21 (FGF21), Epidermal Growth Factor (EGF), Insulin-like Growth Factor-1 (IGF-1), Insulin-Like Growth Factor-2 (IGF-2), Insulin (IN), Interleukin-4 (IL-4), Interleukin-6 (IL-6), Granulocyte Colony Stimulating Factor (G-CSFs), Granulocyte Macrophage Colony Stimulating Factor (GM-CSF), Hepatocyte Growth Factor (HGF), Macrophage Colony Stimulating Factor (M-CSF), Nerve Growth Factor (NGF), Noggin, Erythropoietin (Epo), Leukemia Inhibitory Factor (LIF), Platelet-Derived Growth Factor (PDGF), Neuregulin-1 (NRG-1), Transforming Growth Factor beta 1 (TGFb1), Transforming Growth Factor beta 3 (TGFb3), and Stem Cell Factor (SCF). Any of these GFs, or combinations of any two or more of these GFs, can be grown in plant seeds and recovered therefrom with intact bioactivity.

In the uses, compositions (including supplements), methods and kits disclosed herein, the plant seed protein can be any plant protein expressed in plant seed, such as one or more of those disclosed above. For example, the plant seed protein can be one or more from the group of proteins consisting of dehydrins, late-embryogenesis abundant proteins, (LEA), cyclophilins, ABA-responsive proteins, globulins, albumins, dehydrins, prolamins, vicilins, glutelins, and zeins.

The recombinant GF in this invention can be any recombinant animal GF. Exemplary GFs include any of the above listed GFs. Any one of these GFs, or combinations of two or more of the GFs, can be included in the compositions.

The compositions can in typical embodiments comprise from about 3% to about 99.9% by weight of one or more seed protein, based on the total weight of the composition, such as about 5% to about 99.9%, about 10% to about 99.9% or about 20% to about 99.9%. The lower end of the range can be in the range from about 3% to about 20%, such as about 3%, about 4%, about 5%, about 6%, about 7%, about 8%, about 9%, about 10%, about 12%, about 14%, about 16%, about 18%, or about 20%. The upper end of the range can be from about 80% to about 99.9%, such as about 90% to about 99.9%, such as about 95% to about 99.9%, such as about 80%, about 85%, about 90%, about 91%, about 92%, about 93%, about 94%, about 95%, about 96%, about 97%, about 98%, about 99%, about 99.5%, about 99.6%, about 99.7%, about 99.8% or about 99.9%.

The compositions can in some embodiments comprise in the range of about 0.1% to about 97% of the one or more GF, in particular a recombinant animal GF, such as in the range from about 0.2%, or from about 0.3% or from about 0.4% or from about 0.5% or from about 1% or from about 5%, to about 97% or to about 95% or to about 90% or to about 85% or to about 80% or to about 75% or to about 70%. In some embodiments, the compositions comprise in the range of about 10% to about 30% of one or more GFs.

A distinct advantage of the compositions described herein is that they are free from animal contamination and also free from endotoxins. The compositions are from non-animal sources, which means that native animal components such as serum, endotoxins and antibiotics are not present in the compositions, and neither are human or animal infectious agents or other endogenous mammalian contamination agents, including for example undesirable GFs or cytokines.

The compositions of the invention are preferably non-animal, i.e. the compositions are from a non-animal source. The compositions are preferably plant-derived, meaning that the compositions are also free from bacterial endotoxins that are produced and released from gram negative bacteria such as *E. coli.*

The production of GFs by molecular farming in plants therefore leads to a highly desirable product. Moreover, by recovering the product (GFs) as a plant extract results in substantially increased yields and reduced production costs. Downstream purification of individual GFs is cost-prohibitive for CCM, but is not necessary for the compositions disclosed herein, since the GFs retain their bioactivity in the plant seed mixture and are ready to be used, e.g. as growth media supplements or in growth media. Surprisingly and advantageously, this leads to improved characteristics of the growth factor supplements, manifested in more active and more stable growth factor, when present in the cell culture media.

As should be apparent from the foregoing, the compositions described herein are particularly useful in the generation of CCM, since the compositions fulfil several important characteristics for their use in cost-effective CCM cultivation. Thus, the GFs in the compositions are stable during prolonged storage, due to the presence of plant seed proteins. Thereby, the compositions can be stored until their use in growth media, with minimal or no loss of bioactivity of the GFs.

The compositions can be stored until use, e.g. for as growth media supplements. The compositions can be added to the media just prior to use (i.e. just prior to use in cell culture) or they can be added to the media as the media is put together. In either case, the compositions can be stored in separate containers, where they are stable for prolonged storage.

The GF compositions can be provided in dry form, e.g. as freeze-dried plant extracts or as dry combinations of GFs or GF extracts and specific plant seed proteins, e.g. one or more of dehydrins, late-embryogenesis abundant proteins, (LEA), cyclophilins, ABA-responsive proteins, globulins, albumins, dehydrins, prolamins, vicilins, glutelins, and zeins.

The GF compositions can alternatively be provided in liquid form, to be added to growth media prior to use. Preferably, such liquid compositions are aqueous, and can optionally include one or more buffering agent, salts or other protein stabilizing agents. The GF compositions can also contain other suitable excipients, including but not limited to glycerol, amino acids, saccharides (monosaccharides and/or polysaccharides), vitamins, and inorganic trace elements.

The compositions can also be added directly to growth media, either in dry or liquid form. Once combined with growth media, the concentration of GFs comprised in the final media can in some embodiments be in the range of 0.000001% (w/v) to about 5% (w/v), preferably in the range from about 0.000001% (w/v) to about 2% (w/v), in the range from about 0.000001% (w/v) to about 1% (w/v), in the range from about 0.000001% (w/v) to about 0.5% (w/v), in the range from about 0.000001% (w/v) to about 0.1% (w/v), in the range from about 0.000001% (w/v) to about 0.05% (w/v) or in the range from about 0.000001% (w/v) to about 0.01% (w/v).

The growth media can comprise nutritional components required to sustain growth of animal cells for the generation of cell culture meat, including one or more of amino acids, including essential amino acids, non-essential amino acids, monosaccharides, vitamins, inorganic ions, trace elements. The growth media may additionally contain somatomedins and/or hormones.

Growth media can be any growth media known in the art for growing animal cell. In general, growth media can be serum-based, for example media based on human serum, cattle serum (calf serum, newborn calf serum and/or fetal bovine serum), or horse serum.

Growth media can also, or alternatively, be artificial/synthetic or designed, i.e. growth media made by the adding together required nutrients, such as vitamins, salts, proteins, carbohydrates, cofactors and dissolved 02 and CO2.

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Throughout the description and claims, the terms "comprise", "including", "having", and "contain" and their variations should be understood as meaning "including but not limited to", and are not intended to exclude other components.

The present invention also covers the exact terms, features, values and ranges etc. in case these terms, features, values and ranges etc. are used in conjunction with terms such as about, around, generally, substantially, essentially, at least etc. (i.e., "about 3" shall also cover exactly 3 or "substantially constant" shall also cover exactly constant).

The term "at least one" should be understood as meaning "one or more", and therefore includes both embodiments that include one or multiple components. Furthermore, dependent claims that refer to independent claims that describe features with "at least one" have the same meaning, both when the feature is referred to as "the" and "the at least one".

It will be appreciated that variations to the foregoing embodiments of the invention can be made while still falling within scope of the invention. Features disclosed in the specification, unless stated otherwise, can be replaced by alternative features serving the same, equivalent or similar purpose. Thus, unless stated otherwise, each feature disclosed represents one example of a generic series of equivalent or similar features.

Use of exemplary language, such as "for instance", "such as", "for example" and the like, is merely intended to better illustrate the invention and does not indicate a limitation on the scope of the invention unless so claimed. Any steps described in the specification may be performed in any order or simultaneously, unless the context clearly indicates otherwise.

All of the features and/or steps disclosed in the specification can be combined in any combination, except for combinations where at least some of the features and/or steps are mutually exclusive. In particular, preferred features of the invention are applicable to all aspects of the invention and may be used in any combination.

The invention is further described by the following non-limiting examples.

EXAMPLES

Example 1: Transformed Barley Plant Expressing EGF in Seeds and Purification A genetically transformed *Hordeum vulgare* barley cultivar was generated with the standard *Agrobacterium tumefaciens* mediated transformation of immature embryos (IE) isolated from barley seeds with a synthesized gene, codon optimized according to codon usage in barley, coding for Epidermal Growth Factor, EGF, cloned into a gene expression cassette driven by a seed specific promoter ensuring high, seed specific expression of the gene.

This was followed by tissue culturing the IE on a suitable media in growth cabinet, selecting the resulting plantlets, transferring them into soil or any suitable growing matrix, growing them under suitable climatic condition, harvesting mature seeds for screening and selection of transformed barley lines with strong production of the target protein EGF with standard protein assay methods such as ELISA or Western blot analysis.

Selected lines were further expanded into second generation and third generation for production of seeds, harvesting the seeds, followed by cleaning the seeds with seed cleaning or seed sorting machine, de-hulling the sorted seeds, sterilizing the de-hulled seeds and milling to fine powder with dry-milling or wet-milling, typically with grain size in the range of 100-400 μm diameter, with optimal grain size around 250 μm diameter, extracting total soluble proteins in extraction buffer, clarifying the extract, selecting specific affinity technology for co-purification of EGF and specific seed proteins, using affinity chromatography, selecting stringent and suitable affinity condition for co-purification of EGF and specific seed proteins, buffer exchange and fill and finish.

For extraction of the barley seed proteins and EGF an extraction buffer such as phosphate buffer 50 mM potassium phosphate, 500 mM NaCl and pH 7.0-8.0, with or without high concentration of protein stabilizing agents for EGF such as mannitol or trehalose, or Tris buffer with 50 mM Tris, 500 mM NaCl and pH 8.0, with or without high concentration of protein stabilizing agents for EGF such as mannitol or trehalose.

For clarification of the extract prior to affinity chromatography the extract is centrifuged at 10° C. for 10 min with 5000× G-force.

Typically, for affinity technology utilized is a batch mode target protein binding or expanded bed adsorption (EBA) column or packed-mode Immobilized Metal Affinity Chromatography (IMAC) with a FPLC instrument using the interaction of nickel and histidine on the histidine-tagged EGF expressed in the endosperm-compartment of the seed. To facilitate the use of packed-mode columns and FPLC, the barley extract is first filtrated prior to loading onto the packed column with tangential flow filtration (TFF). The EGF and the co-purified specific seed proteins are eluted from the column using increasing concentration of imidazole following optimization.

Example 2: Production of Growth Factor Extract

Transgenic plants: barley plants expressing in their seeds heterologous human epidermal growth factor (EGF) were obtained as follows:

The cDNA for 53 aa human EGF (Genebank no. NP 001954.2) was codon optimized with regard to barley codon usage (Genscript, USA) and subsequently used to prepare an expression cassette under the control of the 0.42 kb D-hordein promoter from barley (Genebank no X84368). A 6 aa Histidine tag was fused to the N-terminal of the EGF protein. The native N-terminal D-hordein signal peptide was used to target the recombinant protein to the endoplasmic reticulum. This expression cassette was cloned into a binary vector.

*Hordeum vulgare* L. Cv Golden Promise plants were grown vegetatively for about 65-85 days or until approximately 3-20 days postanthesis. Barley heads were selected and the seeds sterilized with 70% ethanol and 3% sodium hypochlorite for 20 min in rotary shaker and the immature embryos were removed from the seeds and placed on a regeneration media essentially as described by Tingey et al. *Agrobacterium tumefaciens* (AGLO) culture, harboring the EGF binary vector, was pipetted onto each explant (the OD value of the culture used was ~0.7). After removing excess *Agrobacterium tumefaciens* the explants were transferred to fresh regeneration media plates and placed in dark cabinet at 24° C. After 1 day the explants were transferred to a fresh regeneration media supplemented with 30 μg/mL hygromycin B and left there for 4-6 weeks. Regeneration of shoots was essentially done as described by Tingey et al. The calli were transferred to shoot-induction media (SIM) and surviving callus and regenerating shoots transferred to fresh SIM every 2 weeks until small plantlets were formed. The plantlets were then transferred to root-induction media (RIM) with 20 μg/mL hygromycin B and surviving plants potted in soil. All transformants were analysed for expression of recombinant EGF protein.

From each transgenic line four seeds from first seed generation (T1 seeds) were randomly selected for analysis. The seeds were crushed by mechanical force prior to milling in a Retsch MM301 bead mill (Qiagen) in a 96 deep-well microplate format. Water-soluble proteins were extracted from the pulverized seeds by extraction in 500 μL of 50 mM potassium phosphate, pH 7.0. Extraction was performed for 1 h at room temperature by mixing in the bead mill and the crude protein extract clarified by centrifugation at 3000×g for 5 min at 4° C. Clarified extract was collected and used for quantitative analysis of the EGF target protein. The target protein accumulation in the seeds was analysed using a commercially available EGF sandwich ELISA kit according to the manufacturer's instructions. In this experiment the content of the EGF in the seeds was determined to be in the range of 500 mg/kg.

Growth factor extract: A transgenic plant extract was prepared by milling harvested seeds from the obtained transgenic barley plants in a mill to obtain fine powder (flour). Extraction buffer was added (50 mM potassium phosphate pH 7.0) to the milled barley flour in a volume/weight ratio of 5/1 of extraction buffer to milled flour. The resulting solution was stirred for 60 minutes at 4° C. Solids were separated from the liquid extract by centrifugal force, centrifuging at 8300 rpm in a refrigerated Centrifuge (Heraeus Primo R) for more, for 15 minutes, and the supernatant decanted off to a fresh vial. The content of heterologous growth factor of the obtained aqueous extract was analysed by SDS-PAGE and Western blotting with a specific antibody. In this experiment the EGF content was about 0.1% of the protein content of the unpurified extract.

Example 3: Composition of Media

A media composition for culturing of muscle stem cells, referred here to as myoblasts, was generated, containing a basal medium, buffer system, glutamine, serum (or serum alternative), specific growth factors extracted from transgenic plants and additional supplements.

Working with highly pure and defined stem cell medium is a key for successive culturing applications. The basal medium for stem cell culturing must be specifically selected depending on cell types and its intended regulation of cell behaviour, either supporting proliferation or differentiation.

CCM medium is usually divided into two medium types, growth medium (expansion medium) and differentiation medium. The growth medium usually contains higher concentration serum (10%-20%), while differentiation medium contains lower concentration serum (1%-5%) or is completely serum-free. Basal media most commonly used for culturing of myoblasts are (a) DMEM, (b) F-12, (c) RPMI-1640 and (d) MCDB120, or a combination of those.

Growth factors commonly added to growth medium for proliferation are FGFb, IGF-1 and EGF in a concentration between 1-20 ng/ml and growth factors commonly added to differentiation medium are IGF-1, EGF, NRG1 and GDNF in a concentration between 1-20 ng/ml.

Example 4: DMEM with Growth Factor from Barley

An example of a basal medium known to support both growth and differentiation of myoblasts is a high glucose Dulbecco's Modified Eagles Medium (DMEM), containing relevant buffer system and other essential basal elements, including high-concentration glucose, L-glutamine and sodium pyruvate, and is additionally supplemented with serum (FBS, foetal bovine serum or HS, horse serum), ITS (insulin-transferrin-selenium), NAA (non-essential amino-acids), dexamethasone, albumin (BSA), growth factors, and pen/strep (pencilling and streptomycin).

Some variation can be found in the CCM field with regard to combination of the basic medium, serum type, components concentrations and source of growth factors. Preferably the culture medium should be chemically defined, serum free and free of animal source and infection agents.

Growth factors commonly added to growth medium for proliferation of muscle stem cells or satellite cells are FGFb, IGF-1 and EGF in a concentration between 1-20 ng/ml and growth factors commonly added to differentiation medium are IGF-1, EGF, NRG1 and GDNF in a concentration between 1-20 ng/ml.

Example 5: Medium for MSC and ADSC

A media composition for culturing of mesenchymal stem cells (MSC) and adipose-derived stromal cells (ADSC) was generated, containing a basal medium, low glucose, buffer system, glutamine, serum (or serum alternative), specific growth factors extracted from transgenic plants and additional supplements.

Working with highly pure and defined stem cell medium is a key for successful culturing applications. The basal medium for stem cell culturing must be specifically selected depending on cell types and its intended regulation of cell behaviour, either supporting proliferation or differentiation.

Typically, a specific adipogenic medium (differentiation medium), used for generating adipocytes from MSCs and/or ADSCs is commonly based on basal medium DMEM/Ham's F-12 with L-glutamine and 10% serum, and commonly supplemented with other essential elements as penicillin, streptomycin, L-glutamine, ascorbate-2-phosphate, and is additionally supplemented with triiodothyrionine, hydrocortisone, isobutyl-methylxanthine, dexamethasone, rosiglitazone and insulin. Some variation can be found in the combination of the basic expansion medium and the specific adipogenic medium, the serum type, components concentrations and source of growth factors. Preferably the culture medium should be chemically defined, serum free and free of animal source and infection agents.

Growth factors commonly added to growth medium for MCS proliferation are FGFb, IGF-1 and EGF in a concentration between 1-20 ng/ml and growth factors commonly added to adipogenic differentiation medium are IGF-1, EGF, IL-6, LIF, NRG1 and GDNF in a concentration between 1-20 ng/ml.

Example 6: Effect of Co-Purified Barley Seed Proteins in DMEM with EGF on 3T3 Cell Growth A growth factor supplement with barley-produced, 30% pure human epidermal growth factor, or containing 30% EGF and 70% specific barley seed proteins, was added to DMEM media with 2 mM glutamine and 10% Calf Serum composition for cell proliferation assay using 3T3 cells at concentration between 0 to 1 ng/ml media, and incubated for 44 hours at 37° C. As a comparison, the barley-produced, 97% pure human EGF, or 97% EGF and only 3% specific barley seed proteins, was added to media composition, at concentration between 0 to 1 ng/ml media, for cell proliferation assay using 3T3 cells. Cell growth was monitored by measuring optical density at 490 nm, with results as shown in FIG. 1. There was a marked shift in cell growth in the media containing both human EGF and barley seed proteins and in the media containing human EGF alone, but with an OD of 1 being achieved at an EGF concentration about an order of magnitude lower when barley seed proteins were present compared to the same media with highly purified EGF, or 97% EGF and 3% specific barley seed proteins, also purified from the barley.

Example 7: Effect of Co-Purified Barley Seed Proteins in DMEM with FGFb on 3T3 Cell Growth Barley-produced fibroblast growth factor basic with specific plant seed proteins was added to DMEM media with 2 mM glutamine and 10% Calf Serum composition for cell proliferation assay using 3T3 cells. As a reference, barley-produced fibroblast growth factor basic was added to media composition for cell proliferation assay using 3T3 cells without the specific plant seed proteins.

Figure 2:
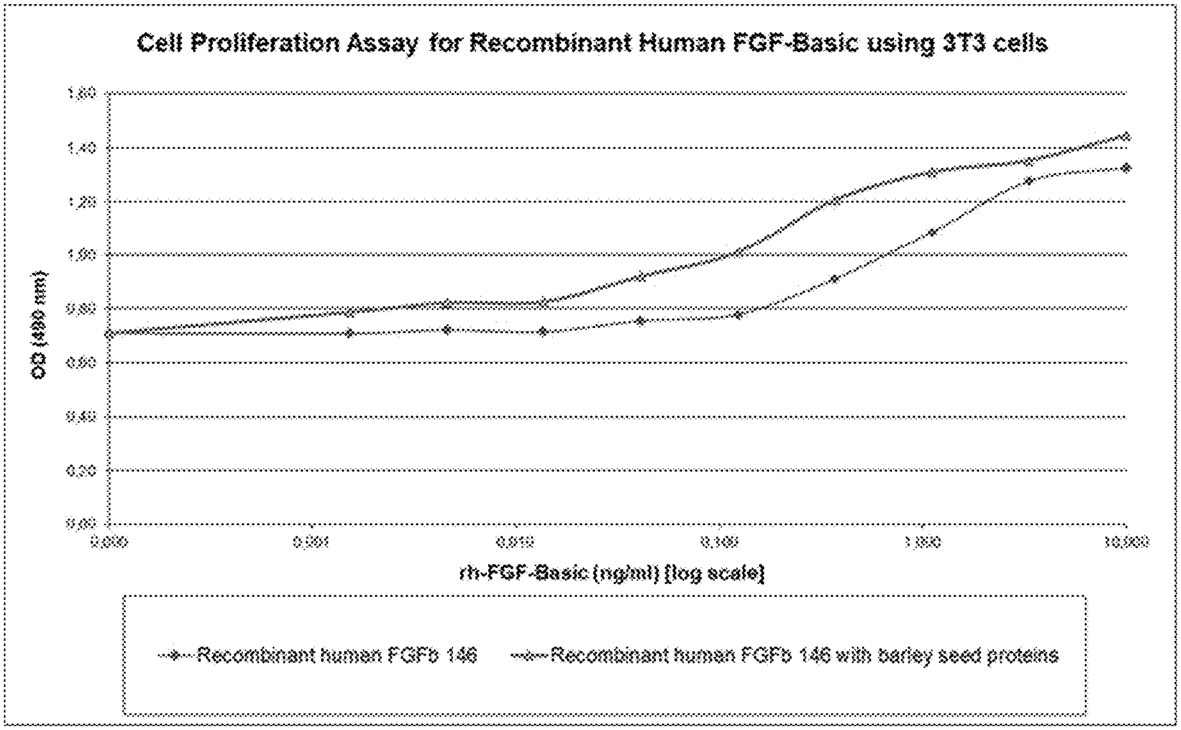
FIG. 2: Results of cell proliferation assay of 3T3 cells grown in medium with plant-expressed human FGF-Basic with and with barley seed proteins.

Cell growth was monitored by measuring optical density at 490 nm, with results as shown in FIG. 2. Again, there was a marked shift in cell growth in the media containing human FGFb and barley seed proteins, with an OD of 1 being achieved at an FGFb concentration about an order of magnitude lower when barley seed proteins were present with the FGFb, in the ratio of 25% FGFb and 75% barley seed proteins, compared to the media minor level of barley seed proteins, or in the ratio of 97% FGFb and 3% barley seed proteins.

Example 8: Effect of Co-Purified Barley Seed Proteins in DMEM with IGF-1 on FDC-P1 Cell Growth A growth factor supplement with barley-produced insulin-like growth factor 1 (IGF-1) with 25% or 5% purity of the IGF-1, or the ratio 25% IGF-1 and 75% specific barley seed proteins, and 5% IGF-1 and 95% specific barley seed proteins, respectively, was added to DMEM media composition with 1% FBS and 10 μg/ml IL-3 for cell proliferation assay using FDC-P1 cells, and compared to *E. coli*-produced IGF-1 growth factor with 98% purity, as a reference.

Figure 3:
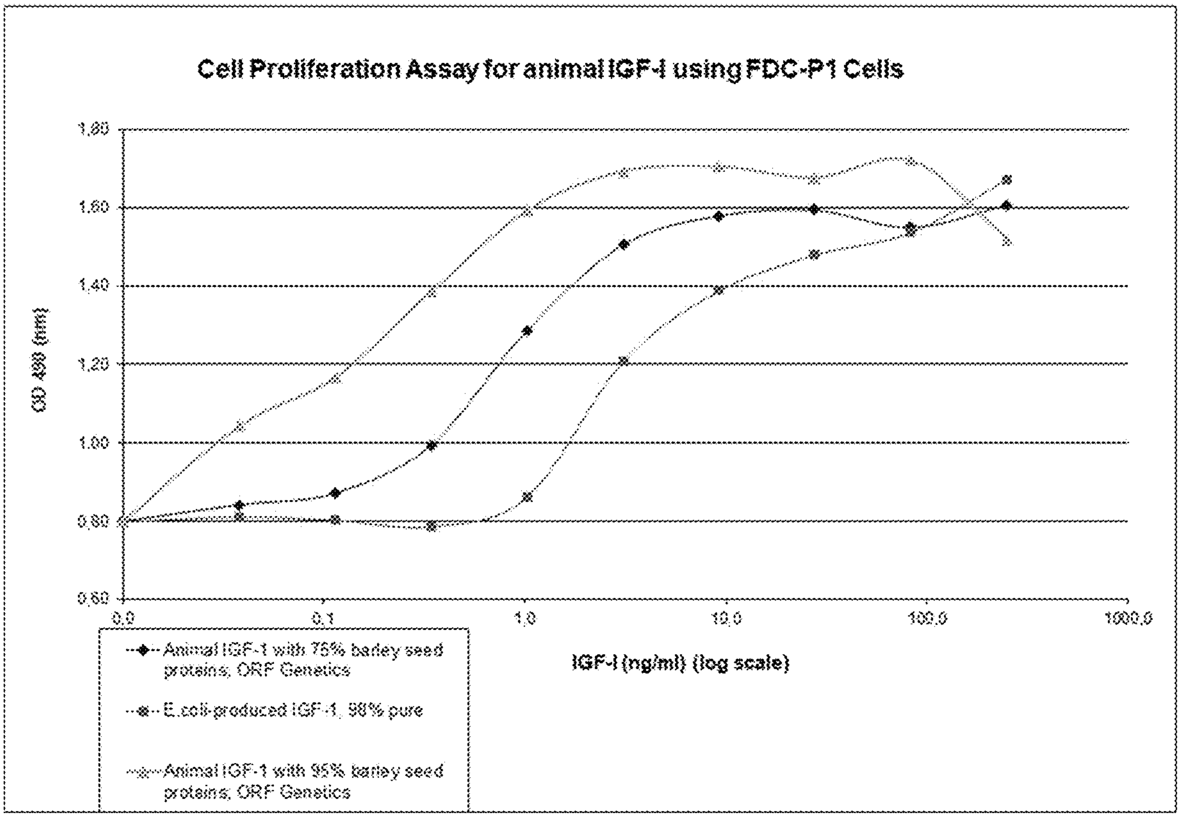
FIG. 3: Results from cell proliferation assay of FDC-P1 cells in medium with barley produced IGF-1 supplement with different amount of barley seed proteins. *E. coli* produced IGF-1 used as comparison.

Cell growth was monitored by measuring optical density at 490 nm, with results as shown in FIG. 3. Again, there was a marked shift in cell growth in media containing both human IGF-1 and barley seed proteins, compared with *E. coli*-produced IGF-1, with an OD of 1 being achieved at an IGF-1 concentration about an order of magnitude lower when barley seed proteins were present at 75%, and two orders of magnitude when barley seed proteins were present at 95%, respectively. Similar results were obtained when the experiment was repeated using DMEM with 1% FBS and 10 μg/mL murine IL-3.

Figure 4:
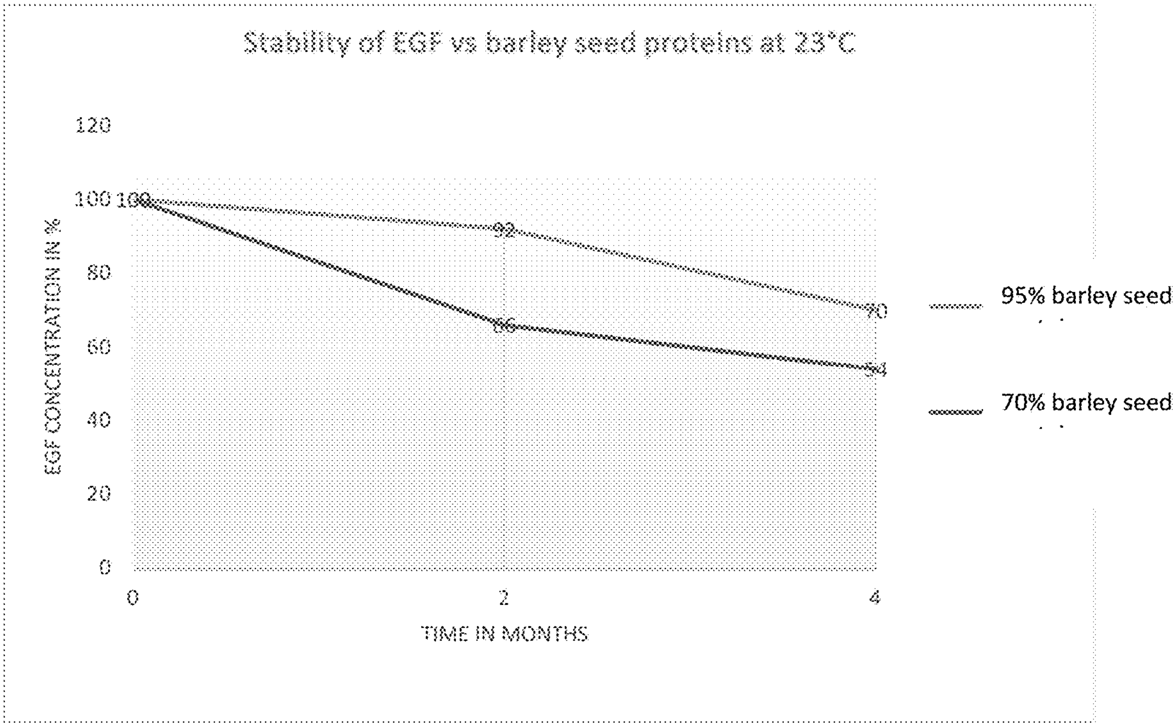
FIG. 4: Stability of EGF in supplement with different concentration of Barley seed proteins.

Example 9: Stability of EGF with Different Concentration of Barley Seed Proteins in Supplement Barley-produced EGF supplement with different concentration of specific barley seed proteins, more specifically with 95% and 70% barley seed proteins, respectively, in the supplement, the remainder being the barley-produced EGF. FIG. 4. The supplements were stored at room temperature (23° C.) in 48% glycerol and 0.5% NaCl. Stability (remaining EGF) was assayed after 2 and 4 months. The less concentrated supplement, that is the supplement with 95% plant protein shows markedly higher stability, with 93% EGF remaining after 2 months and 70% remaining after 4 months, compared to 66% and 54%, respectively, for the supplement with 70% plant proteins. Results are shown in FIG. 4.

Example 10: Characterization of EGF Supplement Composition

Figure 5:
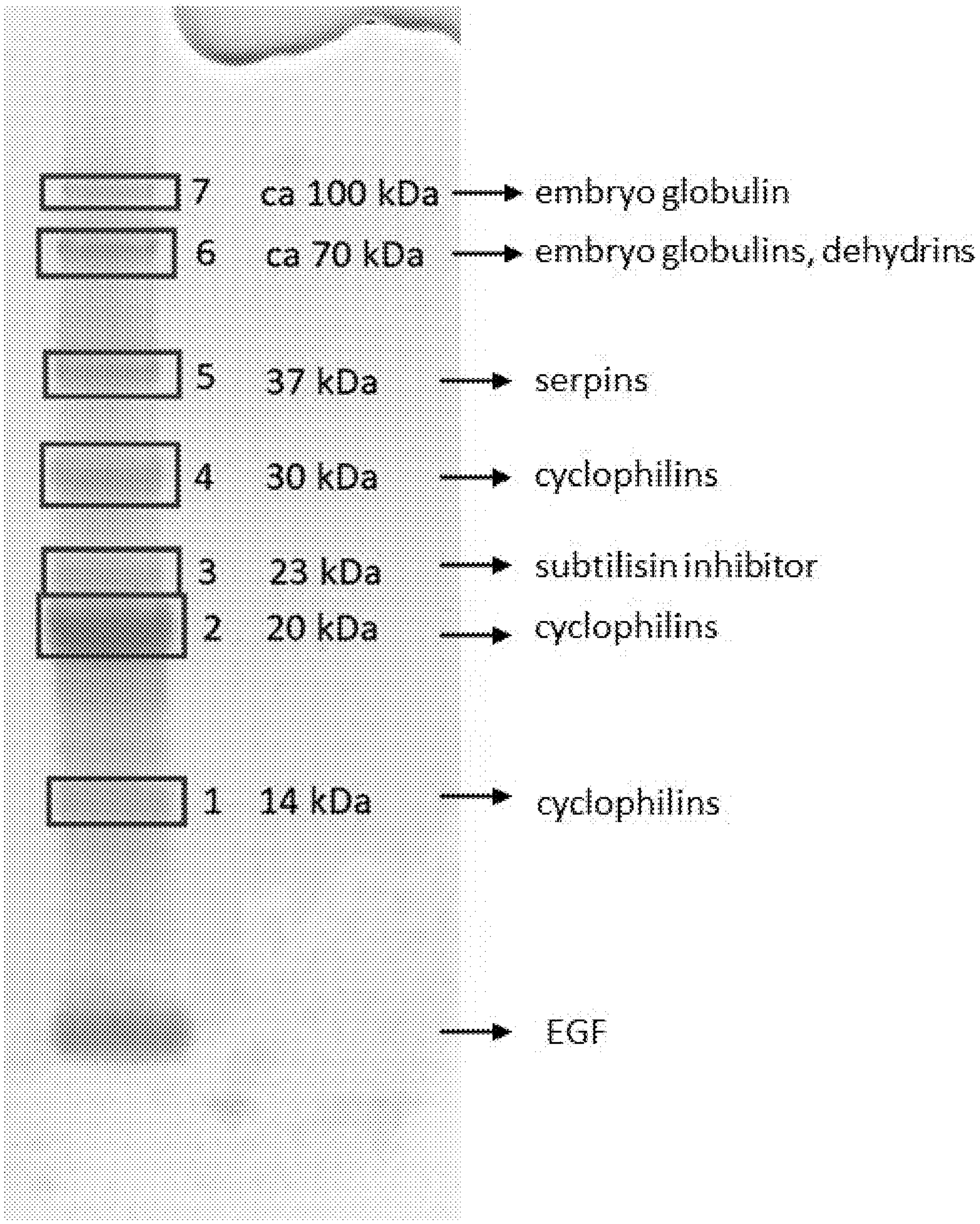
FIG. 5: Stained electrophoresis gel showing composition of EGF supplement.

Harvested barley seeds producing EGF were dried, cleaned in seed sorting machine, de-hulled and then sterilized before milled to fine powder, total water-soluble proteins extracted from the milled powder in 50 mM potassium phosphate, 500 mM NaCl and pH 7.0-8.0, followed by clarification in centrifuge at 10° C. for 10 min with 5000×G force before purification with IMAC affinity chromatography. The eluted proteins include 30% EGF and 70% native barley seed proteins. The EGF and the co-purified native barley seed proteins where eluted from the column and 10 uL sample in loading buffer loaded on 12% Nupage Bis-Tris gel and run for 45 min at 200V, followed by Coomassie staining. Stained bands where excised and the proteins analysed and identified by in-gel trypsin digestion, followed by mass spectrometry (MS) analysis. The proteins identified in addition to the EGF include embryo globulins, dehydrins, serpins, cyclophilins and subtilisin inhibitor as shown in FIG. 5.

Example 11: Characterisation of FGFbasic 'Crude' Supplement Composition

Figure 6:
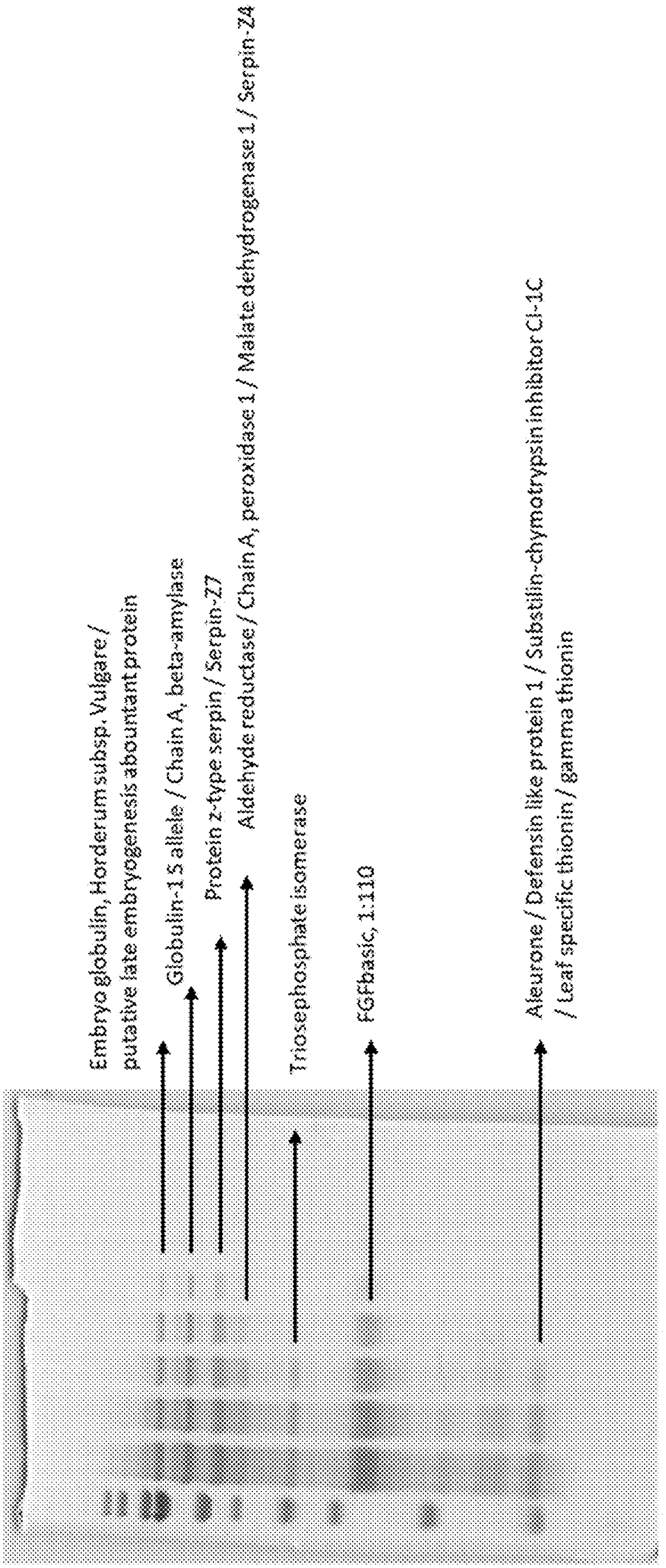
FIG. 6: Stained electrophoresis gel showing composition of FGF basic supplement.

Harvested barley seeds producing FGFb were dried, cleaned in seed sorting machine, de-hulled and then sterilized before milled to fine powder, total water-soluble proteins extracted from the milled powder in 50 mM Tris, 500 mM NaCl, 10 mM 2-mercaptoethanol, pH 8.0, followed by clarification in centrifuge at 10° C. for 10 min with 5000×G force before purification with IMAC affinity chromatography. The EGF and the co-purified native barley seed proteins where eluted from the column and 10 uL sample in loading buffer loaded on 12% Nupage Bis-Tris gel and run for 45 min at 200V, followed by Coomassie staining. The eluted proteins include 30% FGFb and 70% native barley seed proteins. Stained bands where excised and the proteins analysed and identified by in-gel trypsin digestion, followed by mass spectrometry (MS) analysis. The proteins identified in addition to the FGFb include embryo globulins, LEA, beta-amylase, serpins, subtilisin inhibitors, thionins and defensins. as shown in FIG. 6.

Figure 7:
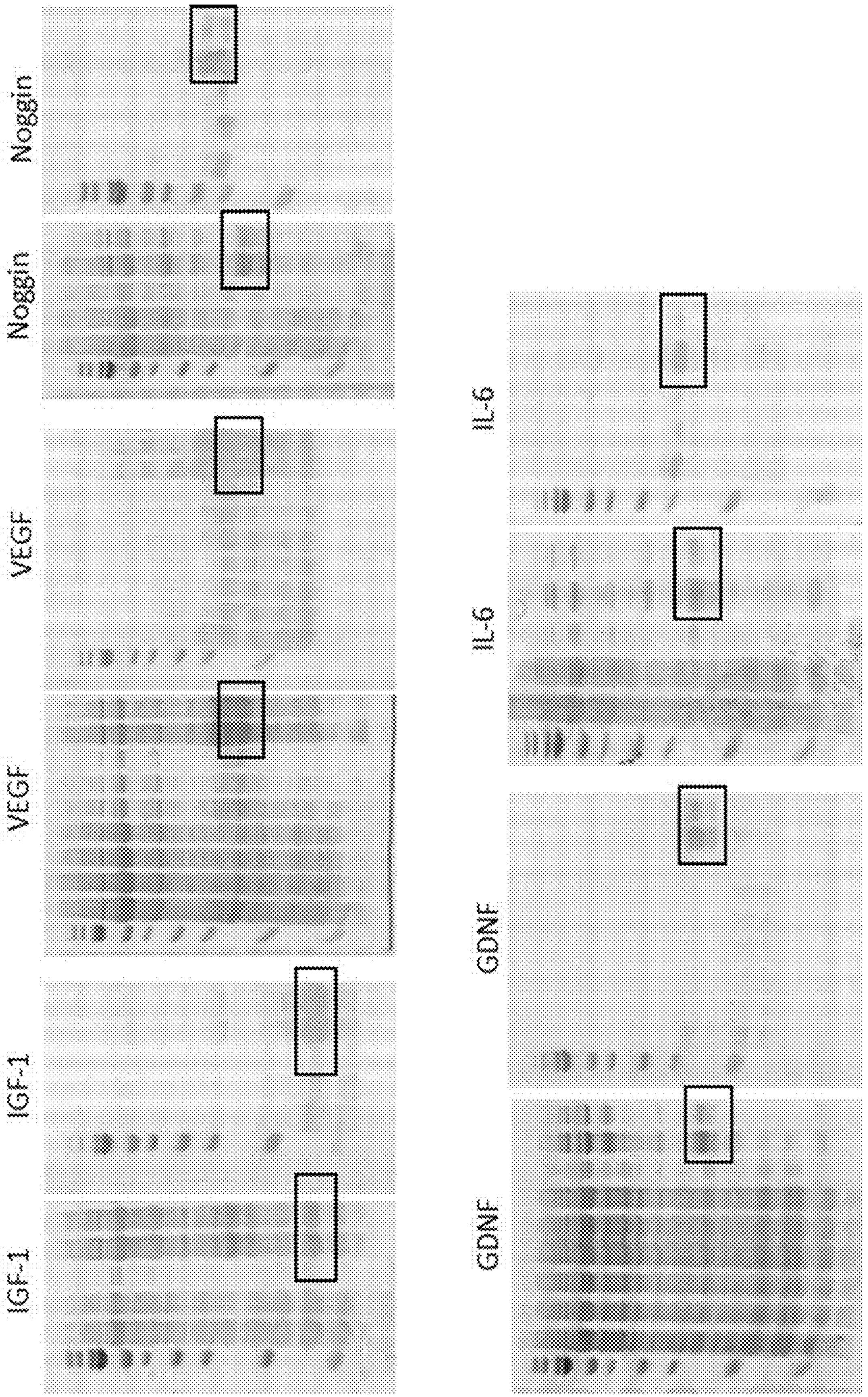
FIG. 7: Five different growth factors expressed in barley seed, with other barley seed proteins.

Example 12: Different Growth Factors Expressed in Barley Seed, with Other Barley Seed Proteins Harvested barley seeds from five different transgenic barley lines expressing five different growth factors where dried; these comprised, respectively, insulin-growth factor 1 (IGF-1), vascular epithelial growth factor (VEGF), Noggin, Glial-derived Neurotropic Factor (GDNF) and Interleukin-6 (IL-6). The seeds from each line were cleaned in seed sorting machine, de-hulled and then sterilized before milled to fine powder, total water-soluble proteins extracted from the milled powder in 50 mM potassium phosphate, 500 mM NaCl and pH 7.0-8.0, followed by clarification in centrifuge at 10 Celsius for 10 min with 5000 G-force before purified with IMAC affinity chromatography. The eluted proteins include in each case the respective growth factor in the range of 10% to 30% and native barley seed proteins in the range of 70% to 90%, respectively. The growth factors and the co-purified native barley seed proteins where loaded on eight separate 12% Nupage Bis-Tris gel and run for 45 min at 200V, followed by Coomassie staining. Samples of each growth factor and the co-purified native barley seed proteins were also loaded on a separate 12% Nupage Bis-Tris gel and run for 45 min at 200V for Western blot analysis, using polyclonal goat anti-mouse immunoglobulins/HRP or polyclonal goat anti-mouse immunoglobulins/HRP for detection, as shown in FIG. 7.

SPECIFIC EMBODIMENTS

1. Use of a growth factor composition comprising one or more recombinant animal growth factor and one or more plant seed protein for cultivating cells for the production of cell culture meat.
2. The use according to embodiment 1, wherein said one or more plant seed protein is selected from the group consisting of dehydrins, protease inhibitors, hordeins, late-embryogenesis abundant proteins, (LEA), cyclophilins, ABA-responsive proteins, globulins, albumins, prolamins, vicilins, glutelins, and zeins.
3. The use according to embodiment 1 or 2, wherein said recombinant animal growth factor is selected from the group consisting of Keratinocyte Growth Factor (KGF), Vascular Epithelial Growth Factor (VEGF), Fibroblast Growth Factors basic (bFGF), Fibroblast Growth Factors acidic (aFGF), Fibroblast Growth Factor-9 (FGF9), Fibroblast Growth Factor-16 (FGF16), Fibroblast Growth Factor-19 (FGF19), Fibroblast Growth Factor-20 (FGF20), Fibroblast Growth Factor-21 (FGF21), Epidermal Growth Factor (EGF), Insulin-like Growth Factor-1 (IGF-I), Insulin-Like Growth Factor-2 (IGF-2), Insulin (IN), Interleukin-4 (IL-4), Interleukin-6 (IL-6), Granulocyte Colony Stimulating Factor (G-CSFs), Granulocyte Macrophage Colony Stimulating Factor (GM-CSF), Hepatocyte Growth Factor (HGF), Macrophage Colony Stimulating Factor (M-CSF), Nerve Growth Factor (NGF), Noggin, Erythropoietin (Epo), Leukemia Inhibitory Factor (LIF), Platelet-Derived Growth Factor (PDGF), Neuregulin-1 (NRG-1), Transforming Growth Factor beta 1 (TGFb1), Transforming Growth Factor beta 3 (TGFb3), and Stem Cell Factor (SCF).
4. The use according to any one of the preceding embodiments, wherein the growth factor composition comprises in the range from about 3% to about 99.9% by weight of the one or more seed protein.
5. The use according to any one of the preceding embodiments, wherein the growth factor composition comprises in the range from about 0.1% to about 97% by weight of the one or more recombinant animal growth factor.
6. The use according to any one of the preceding embodiments, wherein the growth factor composition is from a non-animal source and preferably produced in a transgenic plant.
7. The use according to any one of the preceding embodiments, wherein the growth factor composition is substantially endotoxin-free.
8. The use according to any of the preceding embodiments wherein the growth factor composition is an extract from transgenic plant seed material selected from the group consisting of barley, wheat, oat, rye, maize, rice, soya, peas, millets, sorghum and rape.
9. The use according to any of the preceding embodiments, wherein said recombinant growth factor and one or more plant seed protein are added to cell culture medium in which cells are to be cultivated.
10. A method of cultivating cells for the production of cell culture meat, the method comprising:

a. providing at least one cell culture that is capable of growing to generate a meat-like tissue, and
b. supplying said at least one cell culture with a growth medium for sustaining growth of said cell culture,
characterised in that said growth medium comprises at least one growth factor composition that comprises one or more recombinant animal growth factor and one or more plant seed protein.

11. The method of the previous embodiment, wherein the concentration of the growth factor in the growth medium is in the range of about 0.000001% (w/v) to about 5% (w/v) and preferably in the range from about 0.000001% (w/v) to about 0.01% (w/v).
12. The method of any one of the previous two embodiments, wherein the one or more recombinant animal growth factor and one or more plant seed protein are provided as a growth factor supplement that is added to the growth medium.
13. The method of the previous embodiment, wherein the amount of the one or more recombinant animal growth factor in the growth factor supplement is in the range of about 0.1% to about 97% by weight.
14. The method of any one of the previous four embodiments, wherein said one or more plant seed protein is/are selected from the group consisting of dehydrins, protease inhibitors, hordeins, late-embryogenesis abundant proteins, (LEA), cyclophilins, ABA-responsive proteins, globulins, albumins, prolamins, vicilins, glutelins, and zeins.
15. The method of any one of the previous five embodiments, wherein said recombinant animal growth factor is selected from the group consisting of Keratinocyte Growth Factor (KGF), Vascular Epithelial Growth Factor (VEGF), Fibroblast Growth Factors basic (bFGF), Fibroblast Growth Factors acidic (aFGF), Fibroblast Growth Factor-9 (FGF9), Fibroblast Growth Factor-16 (FGF16), Fibroblast Growth Factor-19 (FGF19), Fibroblast Growth Factor-20 (FGF20), Fibroblast Growth Factor-21 (FGF21), Epidermal Growth Factor (EGF), Insulin-like Growth Factor-1 (IGF-1), Insulin-Like Growth Factor-2 (IGF-2), Insulin (IN), Interleukin-4 (IL-4), Interleukin-6 (IL-6), Granulocyte Colony Stimulating Factor (G-CSFs), Granulocyte Macrophage Colony Stimulating Factor (GM-CSF), Hepatocyte Growth Factor (HGF), Macrophage Colony Stimulating Factor (M-CSF), Nerve Growth Factor (NGF), Noggin, Erythropoietin (Epo), Leukemia Inhibitory Factor (LIF), Platelet-Derived Growth Factor (PDGF), Neuregulin-1 (NRG-1), Transforming Growth Factor beta 1 (TGFb1), Transforming Growth Factor beta 3 (TGFb3), and Stem Cell Factor (SCF).
16. The method of any one of the previous six embodiments, wherein the growth factor composition is from a non-animal source and preferably produced in a transgenic plant.
17. The method of any one of the previous seven embodiments, wherein the growth factor composition is substantially endotoxin-free.
18. The method of any one of the previous eight embodiments, wherein the growth factor composition is an extract from transgenic plant material selected from the group consisting of barley, wheat, oat, rye, maize, rice, soya, peas, millets, sorghum and rape.
19. A growth factor supplement, in particular a growth factor supplement for use in the cultivation of cells for the production of cell culture meat, the growth factor supplement comprising an extract from transgenic plant material selected from the group consisting of barley, wheat, oat, rye, maize, rice, soya, peas, millets, sorghum and rape.
20. The growth factor supplement of the previous embodiment, wherein said extract comprises in the range from about 0.1% to about 97% by weight of one or more recombinant animal growth factor.
21. The growth factor supplement of any of the previous two embodiments, wherein the extract comprises one or more native plant seed protein selected from the group consisting of dehydrins, protease inhibitors, hordeins, late-embryogenesis abundant proteins, (LEA), cyclophilins, ABA-responsive proteins, globulins, albumins, prolamins, vicilins, glutelins, and zeins.
22. The growth factor supplement of any of the previous three embodiments, wherein the extract comprises in the range of about 3% to about 99.9% of the one or more plant seed protein.
23. The growth factor supplement of any of the previous four embodiments, wherein said recombinant animal growth factor is selected from the group consisting of Keratinocyte Growth Factor (KGF), Vascular Epithelial Growth Factor (VEGF), Fibroblast Growth Factors basic (bFGF), Fibroblast Growth Factors acidic (aFGF), Fibroblast Growth Factor-9 (FGF9), Fibroblast Growth Factor-16 (FGF16), Fibroblast Growth Factor-19 (FGF19), Fibroblast Growth Factor-20 (FGF20), Fibroblast Growth Factor-21 (FGF21), Epidermal Growth Factor (EGF), Insulin-like Growth Factor-1 (IGF-1), Insulin-Like Growth Factor-2 (IGF-2), Insulin (IN), Interleukin-4 (IL-4), Interleukin-6 (IL-6), Granulocyte Colony Stimulating Factor (G-CSFs), Granulocyte Macrophage Colony Stimulating Factor (GM-CSF), Hepatocyte Growth Factor (HGF), Macrophage Colony Stimulating Factor (M-CSF), Nerve Growth Factor (NGF), Noggin, Erythropoietin (Epo), Leukemia Inhibitory Factor (LIF), Platelet-Derived Growth Factor (PDGF), Neuregulin-1 (NRG-1), Transforming Growth Factor beta 1 (TGFb1), Transforming Growth Factor beta 3 (TGFb3), and Stem Cell Factor (SCF).
24. The growth factor supplement of any of the embodiments 19 to 23, which is endotoxin-free.
25. The growth factor supplement of any of embodiments 19 to 24, which is selected from a dry formulation and an aqueous formulation.
26. A method for producing a growth factor supplement in particular for supplementing cell culture medium for cell culture meat production, the method comprising
providing a plant expressing a transgenic animal growth factor in its seeds and growing said plant until obtaining mature seeds,
harvesting said seeds,
cleaning the seeds with seed cleaning or seed sorting machine,
de-hulling the cleaned or sorted seeds,
sterilizing the de-hulled seeds and milling to fine powder,
extracting soluble proteins in extraction buffer,
clarifying the obtained extract,
optionally further purifying said growth factor from the extract.
27. The method of embodiment 26, wherein said transgenic animal growth factor is provided with a affinity tag, and wherein the method comprising affinity purification of said animal growth factor.
28. The method of embodiment 26 or 27, wherein said transgenic animal growth factor is selected from the group consisting of Keratinocyte Growth Factor (KGF), Vascular Epithelial Growth Factor (VEGF), Fibroblast Growth Factors basic (bFGF), Fibroblast Growth Factors acidic (aFGF), Fibroblast Growth Factor-9 (FGF9), Fibroblast Growth Factor-16 (FGF16), Fibroblast Growth Factor-19 (FGF19), Fibroblast Growth Factor-20 (FGF20), Fibroblast Growth Factor-21 (FGF21), Epidermal Growth Factor (EGF), Insulin-like Growth Factor-1 (IGF-1), Insulin-Like Growth Factor-2 (IGF-2), Insulin (IN), Interleukin-4 (IL-4), Interleukin-6 (IL-6), Granulocyte Colony Stimulating Factor (G-CSFs), Granulocyte Macrophage Colony Stimulating Factor (GM-CSF), Hepatocyte Growth Factor (HGF), Macrophage Colony Stimulating Factor (M-CSF), Nerve Growth Factor (NGF), Noggin, Erythropoietin (Epo), Leukemia Inhibitory Factor (LIF), Platelet-Derived Growth Factor (PDGF), Neuregulin-1 (NRG-1), Transforming Growth Factor beta 1 (TGFb1), Transforming Growth Factor beta 3 (TGFb3), and Stem Cell Factor (SCF).

29. The method of any of embodiments 26 to 28, wherein said plant is selected from the group consisting of barley, wheat, oat, rye, maize, rice, soya, peas, millets, sorghum and rape.
30. The method of any of embodiments 26 to 29, further comprising the step of drying said obtained extract.
31. The method of any of embodiments 26 to 30, further comprising mixing said obtained growth factor supplement into a cell culture medium, to obtain a supplemented cell culture medium suitable for cultivating cell culture meat (CCM).
32. A cell culture medium comprising a growth factor supplement as set forth in embodiments 19-25.
33. The cell culture medium of the previous embodiment, wherein the cell culture medium comprises in the range of about 0.000001% (w/v) to about 5% (w/v) of the recombinant animal growth factor, and preferably in the range from about 0.000001% (w/v) to about 0.01% (w/v).
34. A kit comprising
    a. A cell culture medium, in particular a cell culture medium for cultivating cells for the production of cell culture meat; and
    b. A growth factor supplement for sustaining growth of said cells.
35. The kit of the previous embodiment, wherein the cell culture medium and the growth factor supplement are provided in separate containers, to be mixed prior to use.
36. The kit of any one of the previous two embodiments, wherein the growth factor supplement is a growth factor supplement as set forth in any of the embodiments 19-25.

REFERENCES

Pandurangan, M, et. al. (2015) *Appl Microbiolog Biotechnol,* 2015 July; 99(13):5391-5.

Mainali, H. R. et, al. (2017) *Scientific Reports,* 7: 39550 January 2017.

Hoekstra, F. A. et. al. (2001) *Trends in Plant Science*, Vol. 6 No. 9 Sep. 2001.

Kosnik P. E, et. al. (2003). *Functional Tissue Engineering*. Springer, New York, NY Ben-Arye T and Levenberg S (2019) *Front. Sustain. Food Syst.* 3:46.

Specht E A (2018). *Biochemical Engineering Journal* Volume 132, 2018, *Pages* 161-168.

Psault B, et. al. (2007). *Mol Ther.* 2007 May; 15(5):867-77. Review.

Post M J (2012). *Meat Sci.* November; 92(3):297-301.

Dodson M V, et. al (1987). *Tissue Cell.* 1987:19(2):159-66.

Yablonka-Reuveni Z, et. al. (1987). *Dev Biol.* 1987 January; 119(1):252-9.

Dodson M W, et. al. (1986). *J Tissue Culture Methods*, Vol. 10, 4, 233-237.

Blanton J R Jr et. al. (1999). *Muscle Nerve.* 1999 January; 22(1):43-50.

Germani A, et. al (2003) *Am J Pathol.* 2003 October; 163(4):1417-28.

Bogliotti Y S, et. al. (2018). *PNAS*, Feb. 27, 2018, vol. 115, no. 9.

Kadirn I T, et. al. (2015). *Journal of Itegrative Agriculture,* 14(2): 222-233.

Sharma S, et. al. (2015). *J Food Sci Technol.* 2015 December; 52(12):7599-607.

Ribeiro M M et. al. (2010). *Cell Transplant.* 2010; 19(8): 1047-54.

Perry, R L S, et. al. (2000). *Frontier in Bioscience* 5; 750-767.

The invention claimed is:

1. A method of cultivating cells for the production of cell culture meat, the method comprising:
  a. providing at least one cell culture that is capable of growing to generate a meat-like tissue, and
  b. supplying said at least one cell culture with a growth medium for sustaining growth and/or differentiation of said cell culture, characterised in that said growth medium comprises at least one growth factor composition that comprises one or more recombinant animal growth factor and one or more native plant seed protein selected from the group consisting of dehydrins, protease inhibitors, hordeins, late-embryogenesis abundant (LEA) proteins, cyclophilins, ABA-responsive proteins, globulins, prolamins, vicilins, glutelins, and zeins, wherein said growth factor is produced in a transgenic plant and the one or more native plant seed protein are native proteins from said transgenic plant, wherein concentration of the recombinant animal growth factor in the growth medium is in the range from 0.000001% (w/v) to 0.01% (w/v).

2. The method of claim 1, wherein the growth factor composition is provided as a growth factor supplement that is added to the growth medium.

3. The method of claim 1, wherein said recombinant animal growth factor is selected from the group consisting of Keratinocyte Growth Factor (KGF), Vascular Epithelial Growth Factor (VEGF), Fibroblast Growth Factors basic (bFGF), Fibroblast Growth Factors acidic (aFGF), Fibroblast Growth Factor-9 (FGF9), Fibroblast Growth Factor-16 (FGF16), Fibroblast Growth Factor-19 (FGF19), Fibroblast Growth Factor-20 (FGF20), Fibroblast Growth Factor-21 (FGF21), Epidermal Growth Factor (EGF), Insulin-like Growth Factor-1 (IGF-I), Insulin-Like Growth Factor-2 (IGF-2), Insulin (IN), Interleukin-4 (IL-4), Interleukin-6 (IL-6), Granulocyte Colony Stimulating Factor (G-CSF), Granulocyte Macrophage Colony Stimulating Factor (GM-CSF), Hepatocyte Growth Factor (HGF), Macrophage Colony Stimulating Factor (M-CSF), Nerve Growth Factor (NGF), Noggin, Erythropoietin (Epo), Leukemia Inhibitory Factor (LIF), Platelet-Derived Growth Factor (PDGF), Neuregulin-1 (NRG-1), Transforming Growth Factor beta 1 (TGFb1), Transforming Growth Factor beta 3 (TGFb3), and Stem Cell Factor (SCF).

4. The method of claim 1, wherein the growth factor composition is an extract from transgenic plant material selected from the group consisting of barley, wheat, oat, rye, maize, rice, soya, peas, millets, sorghum and rape.

* * * * *